May 17, 1960 | E. G. FISHER | Plant Pat. 1,945
ROSE PLANTS
Filed May 5, 1959
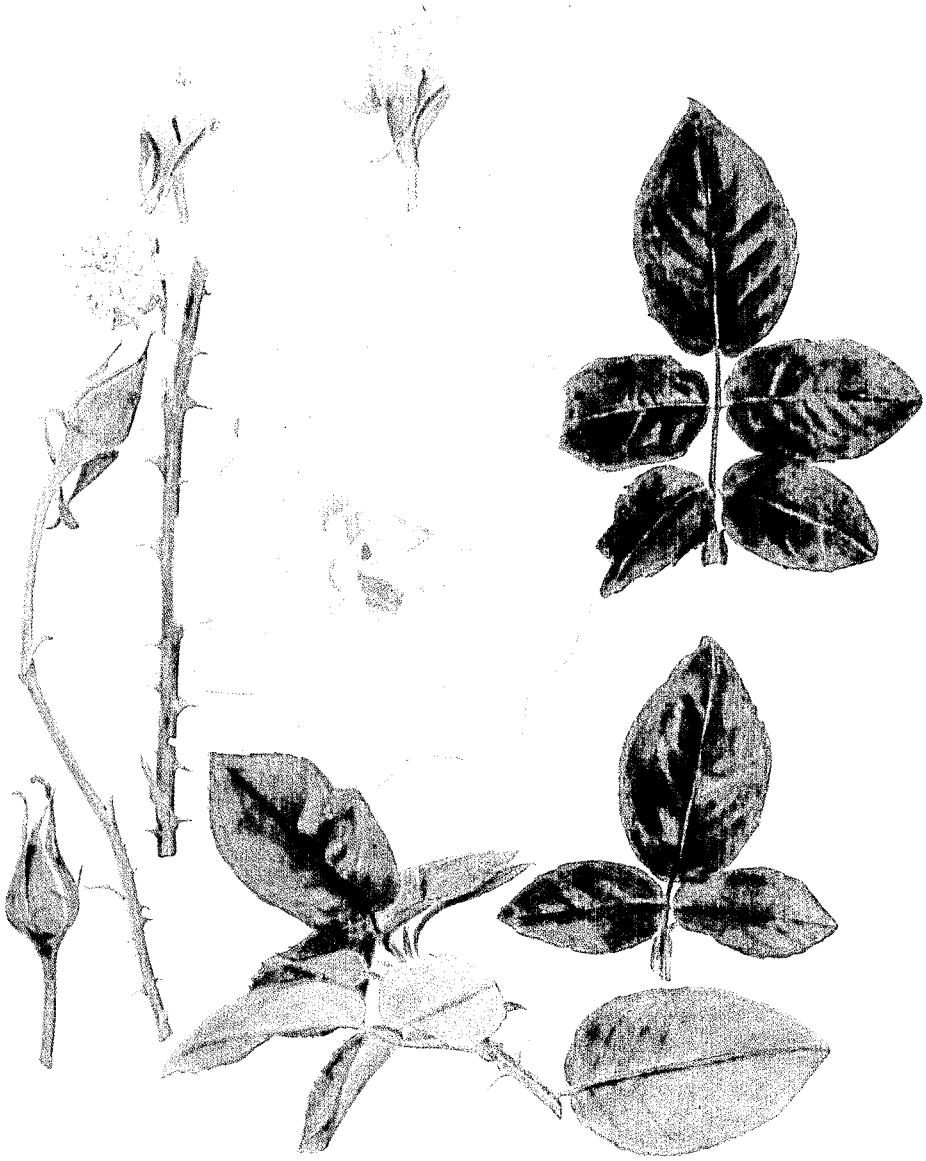
Inventor
Esther Gladys Fisher
Smucker & Mathis
Attorneys United States Patent Office Plant Pat. 1,945
Patented May 17, 1960

1,945

ROSE PLANT

Esther Gladys Fisher, Woburn, Mass., assignor to The Conard-Pyle Company, West Grove, Pa., a corporation of Pennsylvania Application May 5, 1959, Serial No. 811,243

1 Claim. (Cl. 47—61)

The present invention relates to a new and distinct variety of rose plant of the hybrid tea class, which was originated by me by crossing the variety Peace (Plant Patent No. 591) with the variety Orange Nassau (Plant Patent No. 350).

The primary objective of this breeding was to produce a new rose variety which would combine the vigor, bloom form and other desirable characteristics of Peace with the copper-orange color tones of Orange Nassau.

As a result of this breeding, I have produced a new rose variety which is distinctly different from both its parents, as well as all other varieties of its class of which I am aware, as evidenced by the following characteristics which are outstanding and which in combination are unique:

(1) The Rose Opal general color tonality which is suffused with Empire Yellow around the margin of the flower with the center showing Aureolin 3;

(2) The glossy green foliage;

(3) The bushy well branched habit of growth;

(4) The graceful long pointed bud.

Asexual reproduction of my new variety at West Grove, Pennsylvania, shows that the aforementioned characteristics come true to form and are established and transmitted through succeeding propagations.

The accompanying drawing shows typical specimens of the growth and flower of my new variety in different stages of development and as depicted in color as nearly true as it is reasonably possible to make the same in color illustration of this character.

The following is a detailed description of my new variety with color terminology in accordance with the Horticultural Color Chart of the Royal Horticultural Society:

Type: Hardy; bush; outdoor; seedling; for garden decoration.

Class: Hybrid tea.

Breeding: Seedling.

*Seed parent.*—Peace.

*Pollen parent.*—Orange Nassau.

Propagation: It does hold its distinguishing characteristics through succeeding propagations by budding.

*Flower*

Locality where grown: West Grove, Pennsylvania.

Flowers borne: Singly, sometimes two, three or four to stem; normal; medium stems.

Quantity of bloom: Free outdoors.

Continuity: Continuous.

Fragrance: Moderate; tea.

Bud:

*Penduncle.*—Medium; erect stiff; Lettuce Green 861/3 overlaid with Garnet Brown 00918/3; rough; numerous hairs; brown.

*Before calyx breaks.*—Size—Medium large. Form—long pointed with a conspicuous neck; with foliaceous appendages on the surface of the bud; with slender bristle-like foliaceous parts extending beyond the tip of the bud equal to ¼ or more of its length.

*As calyx breaks.*—Color—Currant Red 821.

*As first petal opens.*—Size—medium large. Form—long pointed. Color: outside—a thin margin of Rose Madder 23/2 at outer edge of petal surrounding, over upper half of petal, Straw Yellow 604/2 and over lower half of petal, Chinese Yellow 606/1 at times overlaid with Saturn Red 13/2. Basal area Empire Yellow 603; inside—upper half petal Rose Opal 022/1 streaked with Empire Yellow 603 grading to Lemon Yellow 4 over lower half of petal occasionally tinted with Lemon Yellow 4/2.

*Opening.*—It does open up well.

Bloom:

*Size when fully open.*—Large, 4¼ inches to 4½ inches.

*Petalage.*—Double; from 20 to 25 petals; arranged regularly.

*Form.*—High centered at first; becoming open cupped; petals remaining at first loosely rolled outward; becoming later at maturity loosely rolled outward.

Petals: Thick leathery; with inside satiny; outside shiny.

*Shape.*—Outer — obovate. Intermediate — obovate. Inner—obovate.

This description of a newly opened flower was made from a rose grown outdoors in October, 1958, at West Grove, Pennsylvania.

*Color.*—Outer petal: outside surface—a thin margin of Neyron Rose 623/2 surrounding Chrome Yellow 605/2 over upper half of the petal. Lower half of petal Mimosa Yellow 602/1; inside surface—Rose Opal 022/1 over upper ⅓ of petal becoming streaked with Empire Yellow 603/1 over center ⅓ grading to Aureolin 3/1 over basal ⅓ of petal. Intermediate petal: outside surface—Chrome Yellow 605/2 margined with Neyron Rose 623/2 over upper half of petal grading to Mimosa Yellow intermediate between 602 and 602/1 over lower half of petal; inside surface—Rose Opal 022/1 grading to Claret Rose 021 lightly striped with Aureolin 3 which color covers the basal ⅓ of the petal. Inner petal: outside surface—Chrome Yellow 605/1 over upper half of petal grading to Straw Yellow 604; inside surface—Scarlet intermediate between 19 and 19/1 over upper half of petal becoming washed with and grading into Aureolin 3.

This description was made from a rose that was open for three days, outdoors in October 1958, at West Grove, Pennsylvania.

*Color.*—Outer petal: outside surface—Amber Yellow 505/2 grading to Mimosa Yellow 602/1; inside surface—Crimsom 22/2 washed with 22/3 grading to Mimosa Yellow 602/1 shaded with Aureolin 3. Inner petal: outside surface—Amber Yellow 505/2 grading to Mimosa Yellow 602/1; inside surface—Spinel Red 0023 over upper half of petal becoming washed with and grading into Mimosa Yellow 602/1 shaded with Aureolin 3.

*General color effect.*—Newly opened flower—Rose Opal 022/1 suffused with Empire Yellow 603/1. Three days open—Crimson 22/2 suffused with Mimosa Yellow 602/1, with center of bloom Mimosa Yellow 602/1 shaded with Aureolin 3.

*Behavior.*—Drop off cleanly.

*Flower longevity.*—On bush in garden 3 days in October; cut roses grown outdoors kept at living room temperatures 3 days in October.

*Reproductive organs*

Stamens: Many; arranged regularly about pistils.

Filaments: Most with anthers; long. Color—Primrose Yellow 601/1 at base grading to Chinese Yellow 606 and to Fire Red 15/2 at tip.

Anthers: All open at once; medium. Color—Aureolin 3. Occasionally an anther fused with a petaloid.

Pollen: Moderate to abundant; gold.

Pistils: Medium.

Styles: Uneven; medium long, medium heavy; bunched.

Stigma: White-yellow.

Ovaries: Some protruding from receptacle.

Hips: None observed.

Sepals: Permanent; medium; spear shaped.

Seeds: None observed.

*Plant*

Foliage:

*Leaves.*—Compound of 5 leaflets; abundant; moderately large; leathery glossy.

*Leaflets.*—Shape—oval with apex acute, base obtuse, margin simply serrate.

*Color.*—Mature: upper surface—Parsley Green 00962; under surface—Lavender Green 000761/1. Young: upper surface—Spinach Green 0960 with a narrow margin of Oxblood Red 00823; under surface—Sage Green 000861/1 overlaid with Oxblood Red 00823.

*Rachis (the supporting stem of the compound leaf).*—Medium. Upper side—grooved hairy. Under side—sparsley prickly.

*Stipules.*—Moderately long; medium wide; medium points; turning out at an angle of more than 45°.

*Disease.*—Resistance comparable to the average variety growing under the same cultural conditions.

Growth:

*Habit.*—Bushy upright much branched.

*Growth.*—Free.

*Canes.*—Medium.

*Main stems.*—Bright. Color—Lettuce Green 861. Prickles—several; color—Garnet Brown 00918/3. Hairs—none.

*Branches.*—Bright. Color—Fern Green 0862. Prickles—several; color—Garnet Brown 00918/3. Hairs—none.

*New shoots.*—Dull. Color—Purple Madder 1028. Prickles—several; color—Purple Madder 1028. Hairs—none.

I claim:

A new and distinct variety of rose plant of the hybrid tea class, substantially as herein shown and described, characterized particularly as to novelty by the Rose Opal suffused with Empire Yellow general coloration which is strongly contrasted by the Aureolin color which covers the center of the open bloom, the glossy green foliage, the bushy well-branched habit of growth.

No references cited.